United States Patent [19]
Chu et al.

[11] Patent Number: 5,849,596
[45] Date of Patent: Dec. 15, 1998

[54] PROCESS FOR DETERMINING THE SMOKE CONTENT OF EDIBLE OIL

[75] Inventors: Yan-Hwa Chu, Hsinchu; Wen-Chung Lin, Pingtung, both of Taiwan

[73] Assignee: Food Industry Research and Development Institute, Taiwan

[21] Appl. No.: 676,571

[22] Filed: Jul. 8, 1996

[51] Int. Cl.$^6$ ............................ G01N 21/75; G01N 33/92
[52] U.S. Cl. ................................................ 436/168; 436/71
[58] Field of Search ........................................ 436/168, 71

[56] References Cited

U.S. PATENT DOCUMENTS 4,594,251  6/1986  Nicholson et al. ..................... 426/262
5,091,116  2/1992  Krishnamurphy et al. ............. 260/409

Primary Examiner—Ponnathapura Achutamurthy
Assistant Examiner—Hankyel T. Park
Attorney, Agent, or Firm—Fish & Richardson P.C.

[57] ABSTRACT

The present invention provides a process for determining the smoke content of an edible oil of a given amount, which comprises heating the edible oil to a temperature necessary to generate smoke; collecting the generated smoke by sulfuric acid; and determining the smoke content of the edible oil by colorimetry through comparing the color index of the collected smoke in sulfuric acid with the pre-established calibration function representing the relationship between the color index and concentration of the edible oil smoke in sulfuric acid.

10 Claims, 1 Drawing Sheet

PROCESS FOR DETERMINING THE SMOKE CONTENT OF EDIBLE OIL

BACKGROUND OF THE INVENTION

1. Field of the Invention

The present invention relates to a process for determining the smoke content of an edible oil, more particularly to a process for determining the smoke content of an edible oil by collecting the smoke with sulfuric acid and measuring the color index of the smoke solution in sulfuric acid.

2. Description of the Prior Art

In Taiwan, the total production of edible oils is about 370 thousand tons per year. Soybean oil is the most dominant edible oil, accounting for about 72% of the total production. Other commercially available and commonly used edible oils include sunflower oil, corn oil, palm oil, peanut oil, rice oil and lard olein, etc. In addition to such single component oils, there are also various kinds of mixed oils in the market.

Generally speaking, people in Western countries use vegetable oils to prepare salad dressings and use animal fats to fry food such as chicken and potatoes. However, Chinese people and the Oriental people of Taiwan, Mainland China, and elsewhere commonly use vegetable oils to fry food. Frying food causes the vegetable oils to heated to temperatures as high as 180° C. to 250° C. Due to the presence of the abundant unsaturated fatty acids, vegetable oils are very unstable upon being heated to such high temperatures, and generate hydroperoxides which are harmful to the human body.

Since the harmful hydroperoxides further decompose to a wide variety of volatiles such as aldehydes, ketones and hydrocarbons, which are present in the form of smoke, observing the quantity of the smoke generated from heating an edible oil is a simple criterion for estimating the stability or quality of the edible oil. However, simply observing the quantity of the smoke is not very scientific.

The inventors of the present invention have intended to determine the edible oil smoke by measuring its weight, however, the smoke spreads around all over the container and is not easily collected, thus resulting in extensive error. Some commercially available smoke analysis instruments utilize the transparency principle to detect the smoke, however, the quantity of the smoke sample has to be very large, resulting in inconvenience.

SUMMARY OF THE INVENTION

Therefore, an object of the present invention is to provide a process for determining the smoke content of a given amount of an edible oil. The edible oil smoke is collected effectively by sulfuric acid. The amount of the edible oil sample for determining the smoke content is not necessarily plenty, the apparatus for the determination is simple, the determination process is simple to employ, and the accuracy is high.

To achieve the above object, the process of the present invention includes the following steps of:

heating the edible oil to a temperature necessary to generate smoke;

collecting the generated smoke by sulfuric acid; and obtaining the smoke content of the edible oil by colorimetry through substituting the color index of the collected smoke in sulfuric acid into a pre-established calibration function representing the relationship between the color index and concentration of the edible oil smoke in sulfuric acid to give the concentration of the collected smoke in sulfuric acid, and then multiplying the concentration of the collected smoke in sulfuric acid by the volume of sulfuric acid used for collecting.

The process for establishing the pre-established calibration function representing the relationship between the color index and concentration of the edible oil smoke in sulfuric acid is achieved by the following steps of:

heating the edible oil for a period of time to a temperature necessary to generate smoke, collecting the generated smoke by an organic solvent which is capable of dissolving the smoke;

removing the organic solvent to obtain residual smoke;

preparing a plurality of smoke solutions in sulfuric acid with various concentrations by dissolving the residual smoke by sulfuric acid;

measuring the color index of each of the smoke solutions in sulfuric acid;

analyzing the color indexes and concentrations of the plurality of the smoke solutions in sulfuric acid by regression analysis; and obtaining the pre-established calibration function representing the relationship between the color index and concentration of the edible oil smoke in sulfuric acid.

According to one aspect of the present invention, the present invention utilizes sulfuric acid to collect the edible oil smoke. The smoke will react with sulfuric acid to form yellow to red color, and the smoke content of the edible oil can be measured by colorimetry.

DETAILED DESCRIPTION OF THE INVENTION

Figure 1:
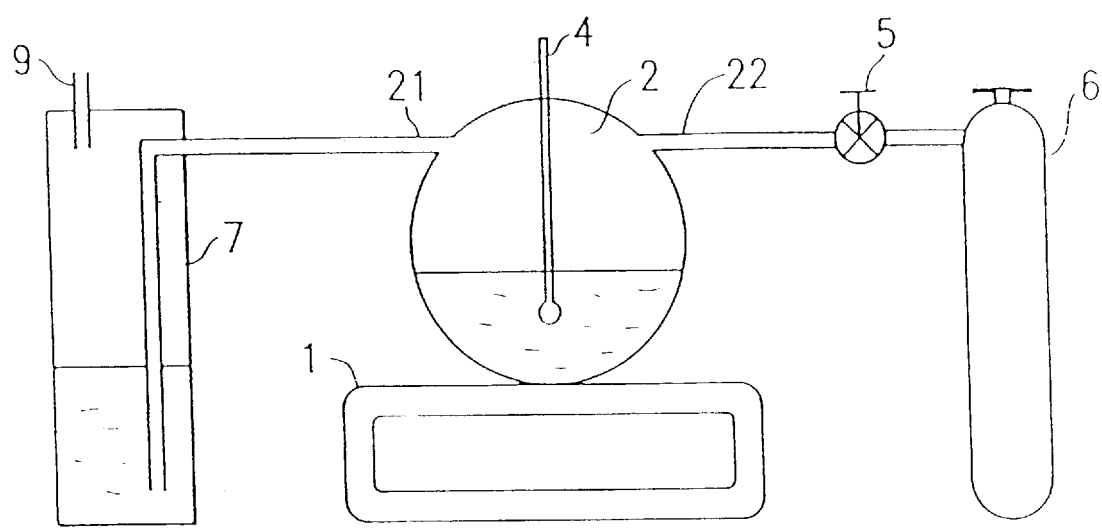
FIG. 1 depicts the apparatus for collecting the smoke of an edible oil according to the present invention.

According to the present invention, before determining the smoke content of a given amount of an edible oil, a calibration function of the smoke content of the edible oil should be first established. The calibration function of the smoke content of the edible oil applied in the present invention represents the relationship between the color index and the concentration of the edible oil smoke solution in sulfuric acid. The apparatus and process for determining the smoke content of a given amount of an edible oil as well as for establishing the calibration function of the smoke content of the edible oil of the present invention are described as follows.

Referring to FIG. 1, a closed container 2 is provided to receive an edible oil and is equipped with a thermometer 4 to measure the temperature of the edible oil. A heating apparatus 1 such as heating plate is provided below or around the closed container 2 for heating. The purpose of the heating is to increase the temperature of the edible oil to a temperature necessary to generate smoke. The closed container 2 is further provided with a gas outlet 21 for expelling the generated smoke. The end of a gas outlet 21 is extended into the inside of a collector 7. The collector 7 is provided for receive a collecting liquid for collecting the generated smoke introduced from the gas outlet 21. In order to collect the generated smoke more efficiently, the closed container 2 is further provided with a gas inlet 22 which is connected with a gas source bottle 6. A gas atmosphere from the gas source bottle 6 is introduced into the closed container 2 via a gas inlet 22 so as to blow the generated smoke. Preferably, the gas outlet 21 is provided on the opposite side of the gas inlet 22, thus once the smoke is generated, it can be blown by the gas atmosphere from the gas inlet 22 and immediately blown into the gas outlet 21. A gas flow control valve 5 is provided on the gas inlet 22 to control the flow rate of the gas atmosphere. A venting means 9 such as a venting tube or valve is provided on the collector 7 for venting the gas atmosphere.

The collecting liquid suitably used in the present invention is any organic solvent, organic acid or inorganic acid which can dissolve the smoke of an edible oil or can dissolve the edible oil itself.

Specifically speaking, the process of establishing the calibration function of the smoke content of the edible oil applies the apparatus shown in FIG. 1 and is described as follows. Referring to FIG. 1, a first portion of an edible oil is charged in the closed container 2 and an organic solvent is charged in the collector 7. The edible oil is heated to a temperature necessary to generate smoke, generally between 200° C. and 300° C. At the same time when heating, a gas atmosphere is introduced from the gas source bottle 6 via the gas inlet 22 to blow the generated smoke. The gas atmosphere suitable for blowing the generated smoke may be any atmosphere which does not deteriorate the generated smoke, for instance, air, nitrogen, helium or argon. The flow rate of the introduced gas atmosphere is controlled by the gas flow control valve 5 at about 5 to 10 ml/sec. The generated smoke will flow into the collector 7 via the gas outlet 21 and will be collected by the organic solvent charged in the collector 7. After heat treatment for a period of time, the collected smoke in the organic solvent is concentrated to remove the solvent and obtain the residual smoke.

The organic solvent used for collecting the edible oil smoke can be any organic solvent which can dissolve the edible oil smoke, that is, generally dissolve the edible oil itself, such as n-hexane.

The residual smoke is divided into several portions. Each portion is weighed and then dissolved with sulfuric acid to prepare a series of edible oil smoke solutions in sulfuric acid with different concentrations. The color index of each of the smoke solutions in sulfuric acid is then measured respectively. The color index and concentration of each smoke solution in sulfuric acid can then be analyzed by mathematical analysis method such as regression analysis, and the calibration function representing the relationship between the color index and concentration of the edible oil smoke in sulfuric acid can be obtained.

The color index of the edible oil smoke in sulfuric acid can be the R value (red value) and Y value (yellow value), as measured by a Lovibond Tintometer. Alternatively, the color index of the edible oil smoke in sulfuric acid can also be the absorbance measured by spectroscopic analysis at a wavelength of 350 nm to 750 nm in the visible light range.

To determine the smoke content of the edible oil, a second portion (another fresh portion) of the edible oil and another clean apparatus shown in FIG. 1 should be used. The fresh portion of the edible oil is charged in the closed container 2, and sulfuric acid rather than an organic solvent is charged in the collector 7. The edible oil is heated to a temperature necessary to generate smoke, generally between 200° C. and 300° C. While heating, a gas atmosphere is introduced from the gas source bottle 6 via the gas inlet 22 to blow the generated smoke. The flow rate of the introduced gas atmosphere is controlled by the gas flow control valve 5 at about 5 to 10 ml/sec. The generated smoke will flow into the collector 7 via the gas outlet 21 and will be collected by sulfuric acid charged in the collector 7. After heat treatment for a period of time, the color index of the collected smoke solution in sulfuric acid is measured and then is substituted into the calibration function representing the relationship between the color index and concentration of the edible oil smoke solution in sulfuric acid obtained from the above mentioned procedures, thus, the smoke content of the second portion of the edible oil can then be calculated.

The edible oil applied to the present invention can be any edible oil including vegetable oils such as soybean oil, sunflower oil, corn oil, palm oil, peanut oil and rice oil, and animal fats such as lard olein, beef tallow and fish oil.

The following examples are intended to demonstrate this invention more fully without limiting its scope, since numerous modifications and variations will be apparent to those skilled in the art.

EXAMPLE 1

Establishment of a Calibration Function of the Smoke Content of soybean Oil Referring to FIG. 1, 200 g of soybean oil was placed in the closed container 2 and n-hexane was placed in the collector 7. The soybean oil was then heated to between 200° C. and 300° C. to generate smoke, and at the same time, an air atmosphere at a flow rate of 5–10 ml/sec was introduced from the gas source bottle 6 into the closed container 2 via the gas inlet 22 to blow the generated smoke. The generated smoke was continuously expelled from the closed container 2 via the gas outlet 21 into the collector 7 and collected by n-hexane. The smoke in n-hexane was concentrated by a rotary evaporator and residual smoke was obtained. 9.05 mg, 18.1 mg, 3.62 mg, 5.43 mg, 7.42 mg, 9.05 mg, 10.86 mg, 12.67 mg of the residual smoke was weighed, dissolved by sulfuric acid to 100 ml, and then measured by a Lovibond Tintometer respectively. The data are shown in Table 1.

TABLE 1

| Sample | Smoke concentration (A): (g/ml) × $10^{-4}$ | Red value (R) | Yellow value (Y) |
|---|---|---|---|
| 1 | 0.905 | 1.0 | 1.4 |
| 2 | 1.810 | 1.4 | 2.6 |
| 3 | 3.620 | 2.5 | 6.1 |
| 4 | 5.430 | 3.4 | 11.1 |
| 5 | 7.240 | 4.2 | 17.0 |
| 6 | 9.050 | 5.5 | 25.5 |
| 7 | 10.860 | 6.3 | 36.5 |
| 8 | 12.670 | 7.5 | 49.0 |

A (the concentration), R value and Y value of the soybean oil smoke solution in sulfuric acid was treated by regression analysis and a calibration function representing the relationship between A, R and Y was obtained:

$$A = -0.95076 + 1.938905R - 0.001653Y$$

EXAMPLE 2

Determination of Soybean Oil Smoke Content

Referring to FIG. 1, 200 g of soybean oil was placed in the closed container 2 and 25 ml of sulfuric acid was placed in the collector 7. The soybean oil was then heated to between 200° C. and 300° C. to generate smoke, and at the same time, an air atmosphere at a flow rate of 5–10 ml/sec was introduced from the gas source bottle 6 into the closed container 2 via the gas inlet 22 to blow the generated smoke.

The generated smoke was continuously expelled from the closed container 2 via the gas outlet 21 into the collector 7 and collected by sulfuric acid. The generated smoke was collected by sulfuric acid every five minutes, and was collected in a fresh clean collector 7 charged with fresh sulfuric acid each time. The total heating and collecting time was 15 minutes.

Totally five runs were repeated to collect the generated smoke by sulfuric acid every five minutes. Each of the smoke solutions in sulfuric acid was determined on a Lovibond Tintometer to measure the R value and Y value. The R value and Y value are then substituted into the calibration function obtained from Example 1 to give the A value (the concentration). The smoke content was calculated out from multiplying the A value by the volume of sulfuric acid (25 ml). The results are shown in Table 2. The average smoke content of 200 g of soybean oil heated for 15 minutes is 0.0356 ±0.0039 g.

However, it should be noted that the kind of the edible oil used, the weight of the edible oil used will influence the coefficients of the calibration function obtained from Example 1. Therefore, when determining the smoke content of an edible oil different from soybean oil or determining the smoke content of different weights of soybean oil, a calibration function representing the color index (R value, Y value) and the concentration of the smoke in sulfuric acid should be re-established.

TABLE 2

|  | R value | Y value | Smoke concentration (A): (g/ml) × $10^{-4}$ | Smoke content ($10^{-4}$ g) |
|---|---|---|---|---|
| 1st run |  |  |  |  |
| 0–5 min | 0.9 | 1.9 | 0.763 | 19.071 |
| 5–10 min | 3.3 | 13.9 | 5.218 | 130.446 |
| 10–15 min | 5.0 | 26.5 | 8.306 | 207.643 |
| Total |  |  |  | 357.161 |
| 2nd run |  |  |  |  |
| 0–5 min | 1.0 | 2.4 | 0.948 | 23.712 |
| 5–10 min | 3.9 | 10.1 | 6.312 | 157.794 |
| 10–15 min | 5.5 | 33.0 | 9.168 | 229.193 |
| Total |  |  |  | 410.699 |
| 3rd run |  |  |  |  |
| 0–5 min | 1.1 | 3.1 | 1.131 | 28.270 |
| 5–10 min | 3.4 | 16.0 | 5.377 | 134.426 |
| 10–15 min | 4.7 | 26.5 | 7.724 | 193.101 |
| Total |  |  |  | 355.797 |
| 4th run |  |  |  |  |
| 0–5 min | 0.9 | 2.2 | 0.758 | 18.947 |
| 5–10 min | 3.11 | 2.7 | 4.850 | 121.248 |
| 10–15 min | 4.02 | 0.5 | 6.466 | 161.650 |
| Total |  |  |  | 301.845 |
| 5th run |  |  |  |  |
| 0–5 min | 1.0 | 2.5 | 0.947 | 23.671 |
| 5–10 min | 3.2 | 13.6 | 5.029 | 125.723 |
| 10–15 min | 4.9 | 25.5 | 8.128 | 203.209 |
| Total |  |  |  | 352.603 |

EXAMPLE 3

Determination of Sunflower Oil Smoke Content

The same procedures for establishing a calibration function and for determining the smoke content as described in Examples 1 and 2 were employed, except that soybean oil was replaced by sunflower oil. The result is that the average smoke content of 200 g of sunflower oil heated for 15 minutes is 0.0223±0.0004 g. Table 3 compares the smoke content of soybean oil and that of sunflower oil.

TABLE 3

| Oil | Smoke content (g) | Deviation |
|---|---|---|
| Soybean oil | 0.0356 ± 0.0002 | 0.5 |
| Sunflower oil | 0.0223 ± 0.0004 | 1.7 |

From the above examples, it can be concluded that the edible oil smoke can be collected effectively by sulfuric acid. The amount of the edible oil sample required for determining the smoke content is not necessarily that much, the apparatus for the determination is simple, the determination process is simple to employ, and the accuracy is high. Since the smoke content of an edible oil of a given amount is a criterion for estimating the quality or stability of an edible oil, once the smoke content of an edible oil of a given amount is determined, those skilled in the art can incorporate suitable and effective antioxidants into the edible oil or, alternatively, incorporate other edible oils to reduce the smoke content of the edible oil.

What is claimed is:

1. A process for determining the smoke content of an edible oil, comprising the following steps of:

heating a batch of the edible oil to a temperature necessary to generate smoke;

collecting the generated smoke by sulfuric acid; and obtaining the smoke content of the edible oil by colorimetry through substituting the color index of the collected smoke in sulfuric acid into a pre-established calibration function representing the relationship between the color index and concentration of the edible oil smoke in sulfuric acid to give the concentration of the collected smoke in sulfuric acid, and then multiplying the concentration of the collected smoke in sulfuric acid by the volume of sulfuric acid used for collecting the generated smoke;

wherein the pre-established calibration function representing the relationship between the color index and concentration of the edible oil smoke in sulfuric acid is established by the following steps of:

heating another batch of the edible oil in an identical manner to generate smoke, collecting the generated smoke by an organic solvent which is capable of dissolving the smoke;

removing the organic solvent to obtain residual smoke;

preparing a plurality of smoke solutions in sulfuric acid with various concentrations by dissolving the residual smoke in sulfuric acid;

measuring the color index of each of the smoke solutions in sulfuric acid;

analyzing the color indexes and concentrations of the plurality of the smoke solutions in sulfuric acid by regression analysis; and obtaining the pre-established calibration function representing the relationship between the color index and concentration of the edible oil smoke in sulfuric acid.

2. The process as claimed in claim 1, wherein the color index is the R value (red value) and the Y value (yellow value), as measured by a Lovibond Tintometer.

3. The process as claimed in claim 1, wherein the color index is the absorbance measured by spectroscopic analysis at a wavelength of between 350 nm and 750 nm.

4. The process as claimed in claim 1, wherein the edible oil is heated to a temperature between 200° C. and 300° C.

5. A process for determining the smoke content of an edible oil, comprising the following steps of:
- (a) providing a calibration function of the smoke content of the edible oil, comprising the following steps of:
  - (a1) heating a first batch of the edible oil in a closed container for a period of time to a temperature necessary to generate smoke, and expelling the generated smoke via a gas outlet provided on the closed container, and said heating and expelling steps being employed at the same time;
  - (a2) collecting the generated smoke by an organic solvent which is capable of dissolving the smoke;
  - (a3) removing the organic solvent to obtain residual smoke;
  - (a4) preparing a plurality of smoke solutions in sulfuric acid with various concentrations by dissolving the residual smoke in sulfuric acid;
  - (a5) measuring the color index of the smoke solutions in sulfuric acid;
  - (a6) obtaining the calibration function of the smoke content of the edible oil, which represents the relationship between the concentration and the color index of the edible oil smoke solution in sulfuric acid;
- (b) heating a second batch of the edible oil in an identical manner to generate smoke;
- (c) collecting the generated smoke by sulfuric acid to obtain a smoke solution in sulfuric acid; and
- (d) measuring the color index of the smoke solution in sulfuric acid, and substituting said color index into the calibration function obtained from step (a), to obtain the smoke content of the second batch of the edible oil.

6. The process as claimed in claim 5, said process further comprising a step of introducing a gas atmosphere via a gas inlet provided on the closed container into the closed container to blow the smoke, said introduction step being employed twice and being employed at the same time as steps (a1) and (b) respectively.

7. The process as claimed in claim 6, wherein the gas atmosphere is selected from the group consisting of air, nitrogen, helium and argon.

8. The process as claimed in claim 6, wherein the gas atmosphere is introduced with a flow rate of 5 to 10 ml/sec.

9. An apparatus for collecting the smoke of an edible oil, comprising a closed container for receiving the edible oil, the closed container being provided with a gas inlet which is connected to a gas source and being provided with a gas outlet, the gas source being capable of introducing a gas atmosphere into the closed container via the gas inlet to blow the smoke of the edible oil, which is generated from heating the edible oil, into a collector via the gas outlet, the collector being provided for receiving a collecting liquid whereby the generated smoke can be collected by the collecting liquid, and the collector being provided with a venting means for venting the gas atmosphere.

10. The apparatus as claimed in claim 9, wherein the gas outlet is provided on the opposite side of the gas inlet.

* * * * *